US009518274B2

(12) United States Patent
Delmas et al.

(10) Patent No.: US 9,518,274 B2
(45) Date of Patent: Dec. 13, 2016

(54) PROCESS FOR PRODUCING BIOETHANOL BY ENZYMATIC HYDROLYSIS OF CELLULOSE

(75) Inventors: Michel Delmas, Auzeville-Tolosane (FR); Bouchra Benjelloun Mlayah, Pompertuzat (FR)

(73) Assignee: COMPAGNIE INDUSTRIELLE DE LA MATIERE VEGETALE—CIMV, Levallois Perret (FR)

( * ) Notice: Subject to any disclaimer, the term of this patent is extended or adjusted under 35 U.S.C. 154(b) by 0 days.

(21) Appl. No.: 13/822,972

(22) PCT Filed: Oct. 5, 2011

(86) PCT No.: PCT/EP2011/067391

§ 371 (c)(1),
(2), (4) Date: Mar. 13, 2013

(87) PCT Pub. No.: WO2012/049054

PCT Pub. Date: Apr. 19, 2012

(65) Prior Publication Data

US 2013/0183733 A1  Jul. 18, 2013

(30) Foreign Application Priority Data

Oct. 13, 2010 (FR) .................................... 10 58327

(51) Int. Cl.
*C12P 7/10* (2006.01)
*C13K 1/02* (2006.01)
*A23L 1/30* (2006.01)

(52) U.S. Cl.
CPC ............... *C12P 7/10* (2013.01); *A23L 1/3014* (2013.01); *C13K 1/02* (2013.01); *A23V 2002/00* (2013.01); *C12P 2201/00* (2013.01); *Y02E 50/16* (2013.01)

(58) Field of Classification Search
CPC .................................. D21C 3/20; D21C 3/222

(Continued)

(56) References Cited

U.S. PATENT DOCUMENTS 7,402,224 B1    7/2008  Avignon et al.
2008/0026431 A1  1/2008  Saito et al.
2008/0057555 A1* 3/2008  Nguyen .................... 435/165

FOREIGN PATENT DOCUMENTS

CN    101 787 384 A   7/2010
CN    102 153 763 A   8/2011
(Continued)

OTHER PUBLICATIONS

Wei et al., "Machine Translation of CN102153763", 2011, pp. 1-14.*

(Continued)

*Primary Examiner* — Sharmila G. Landau
*Assistant Examiner* — Sheridan Macauley
(74) *Attorney, Agent, or Firm* — Young & Thompson

(57) ABSTRACT

A process for producing bioethanol includes the steps of pretreatment (consisting in destructuring the lignocellulosic vegetable raw material by placing it in the presence of a mixture containing formic acid, acetic acid and water, then in separating cellulose), of enzymatic hydrolysis and of alcoholic fermentation, characterized in that it includes, prior to the enzymatic hydrolysis, a step of partial elimination of the lignins so as to obtain a residual overall level of lignins (T), expressed as percentage by weight, which is non-zero and which is included in a range determined by a lower limit, and an upper limit Bsup, respectively equal to 0.30% and 4%. In order to obtain conditions of acidification before the enzymatic hydrolysis step, the process includes a step for re-acidification of the mixture, which is carried out with an acid, or of a mixture of acids, of determined pKa, and preferably with weak organic.

16 Claims, 1 Drawing Sheet

(58) Field of Classification Search
USPC .................................................... 435/165
See application file for complete search history.

(56) References Cited

FOREIGN PATENT DOCUMENTS

| JP | 58 098093 | A | 6/1983 |
|---|---|---|---|
| WO | 00/68494 | A1 | 11/2000 |
| WO | 01/32715 | A1 | 5/2001 |
| WO | 2008/065433 | A1 | 6/2008 |
| WO | 2009/092749 | A1 | 7/2009 |
| WO | 2010/006840 | A2 | 1/2010 |
| WO | 2010/060183 | A1 | 6/2010 |

OTHER PUBLICATIONS

Buranov A U et al.: "Lignin in straw of herbaceous crops", Industrial Crops and Products, Elsevier, NL, vol. 28, No. 3, Nov. 1, 2008, pp. 237-259, XP023980748, ISSN: 0926-6690, DOI: 10.1016/J. INDCROP.2008.03.008 [retrieved on Aug. 21, 2008] p. 243, right-hand column, lines 15-18; table 1, Cited in ISR.

Wang et al.: "Sodium hydroxide pretreatment and enzymatic hydrolysis of coastal Bermuda grass.", Bioresource Technology, vol. 101, No. 10, May 2010, pp. 3583-3585, XP002639906, ISSN: 1873-2976, 001: 10.1016/j.biortech.2009.12.097 * abrege; figure 1; tableaux 1, 2 alineas [001.], [2.2J, [2.3], [3.3], Cited in Written Opinion.

Zhao et al.: "Enhanced enzymatic hydrolysis of spruce by alkaline pretreatment at low temperature", Biotechnology and Bioengineering, vol. 99, No. 6, Apr. 2008, pp. 1320-1328, XP002639907, ISSN: 0006-3592, 001: 10.1002/bit.21712 * abrege; figures 3-8; tableau I * * p. 1321, colonne de droite, dernier alinea—p. 1322, colonne de gauche, alinea 2 *, Cited in Written Opinion.

Written opinion dated, Jun. 8, 2011, from corresponding French application.

International Search Report, dated May 23, 2012, from corresponding PCT application.

\* cited by examiner

PROCESS FOR PRODUCING BIOETHANOL BY ENZYMATIC HYDROLYSIS OF CELLULOSE

FIELD OF THE INVENTION

The present invention relates to a process for producing bioethanol, or ethanol, comprising a pretreatment of lignocellulosic vegetable raw material in order to separate the cellulose, and comprising an enzymatic hydrolysis of the cellulose.

BACKGROUND OF THE INVENTION

The applicant, CIMV, is a company specializing in the treatment and economic use of lignocellulosic vegetable raw material.

In this regard, the applicant has filed and is the proprietor of various patent applications and patents relating to a process for producing paper pulp, lignins, sugars and acetic acid by fractionation of lignocellulosic vegetable material in a formic acid/acetic acid medium (WO-A1-00/68494).

The applicant is also the proprietor of patent applications and/or patents relating to a process for pretreating a lignocellulosic vegetable material with a view to producing bioethanol (WO-A2-2010/006840).

Such a pretreatment process makes it possible in particular to obtain, from the lignocellulosic vegetable raw material (LVRM), under economic industrial conditions, firstly a substrate made up essentially of defibred cellulose exhibiting optimum conditions for its subsequent enzymatic hydrolysis, and a second substrate made up of sugar molasses originating from hemicelluloses of which the hydrolysates are devoid of furfural.

The applicant has therefore already proposed a process for producing bioethanol from a lignocellulosic vegetable raw material, comprising the successive steps of pretreatment of the LVRM, of enzymatic hydrolysis of the pretreated material and of alcoholic fermentation of the products resulting from the hydrolysis step.

The applicant has in particular proposed a process for producing bioethanol from a lignocellulosic vegetable raw material, comprising the successive steps of:
a) pretreatment of the lignocellulosic vegetable raw material in order to separate the cellulose, the hemicelluloses and the lignins contained in this lignocellulosic vegetable raw material, the pretreatment comprising the following successive steps consisting in:
  (i) destructuring the lignocellulosic vegetable raw material by placing it in the presence of a mixture containing formic acid and water, at a reaction temperature between 95° C. and 110° C.;
  (ii) then, at atmospheric pressure and prior to any hydrolysis then fermentation action, in separating:
  on the one hand, the solid phase mainly consisting of said cellulose capable of then being hydrolysed and fermented for the production of bioethanol;
  and on the other hand, the liquid phase, containing in particular in a solution of water, the formic acid, the lignins and the hemicelluloses;
b) enzymatic hydrolysis of said solid phase;
c) alcoholic fermentation of the products resulting from said hydrolysis step, which are capable of being fermented for the production of bioethanol.

This process is in particular described in detail in document EP-2 235 254 (WO-A1-2009/092749), to the content of which reference may be made and which is incorporated herein by way of reference.

This process proposes an approach that is radically different from that of the prior art, by carrying out a separation of the three biopolymers by solvolysis in an acid/water medium, which makes it possible to separate linear, non-recombined, low-molecular-weight lignins with a high added value, prior to any action of hydrolysis then of fermentation of the cellulose and of the hemicelluloses.

This process, which makes it possible to obtain industrial performance levels regardless of the nature of the plants used, and which is therefore particularly advantageous in the case of annual plants for opening the way to a new economic use, in particular in the case of cereal straws and sugarcane bagasse or sugar sorghum bagasse, said economic use adding to that already proposed by the applicant in International Application WO-A1-00/68494 which relates to a process for producing paper pulp, lignins, sugars and acetic acid by fractionation of lignocellulosic vegetable material in a formic acid/acetic acid medium.

These inventions (CIMV processes) are aimed at improving the industrial conditions for the production of ethanol or bioethanol from LVRM, and in particular the hydrolysis of cellulose to give fermentable sugars.

Generally and in a known manner, the processes for producing bioethanol from LVRM take into account several parameters.

Among these parameters, it has in particular been identified that lignin can be an enzyme inhibitor and that the lignocellulosic matrix must be pretreated in order to make the cellulose and the hemicelluloses hydrolysable.

By virtue of their chemical composition, lignin polymers are insoluble and highly reactive.

As a result, the presence of lignins reinforces the cellulose-hemicellulose network, and they hinder the penetration and the action of enzymes, requiring the presence of water.

Enzymatic hydrolysis of cellulose is a recommended approach for obtaining fermentable sugars for various reasons, and in particular because the results of economic evaluations are in favour of enzymatic hydrolysis, when it is compared with chemical hydrolysis.

Furthermore, enzymatic hydrolysis generates few effluents to be treated and no corrosion problems.

The actual enzymatic hydrolysis is carried out by simply bringing the pretreated vegetable raw material into contact with an enzymatic solution, while ensuring that the suspension is homogeneous and that optimum conditions are maintained, said conditions being, for example for T. reesei cellulases, a temperature between 45° C. and 50° C. and a pH of about 4.8.

The enzyme action time depends on the amount of enzymes that is used and on the specific activity of the enzymes.

During the enzymatic hydrolysis, the reducing sugars are essentially released in the form of glucose.

The enzymes involved in cellulose degradation, which are commonly called cellulases, are of various types and of various origins and they are characterized in particular by their activity.

The cost of the cellulases is relatively high and constitutes a factor often estimated to be the most expensive in the production of bioethanol from LVRM.

As a result, important efforts have been made to determine the mechanism of enzymatic hydrolysis with a view to improving it, it being a complex process of the action of soluble proteins on an insoluble and "refractory" substrate.

Another parameter of the efficiency and cost-effectiveness of an enzymatic hydrolysis process is the hydrolysis time, which can be relatively long, from 48 to 72 h.

Once the cellulose has been hydrolysed to glucose by enzymatic hydrolysis, the glucose is fermented in the same way as, for example, the glucose resulting from starch.

Known problems specific to the use of LVRM as initial substrate remain, such as the possible presence of toxic compounds and inhibitors resulting from the hemicelluloses and the lignin, and also the possibility of carrying out the enzymatic hydrolysis and the fermentation in a single step.

The inhibitors present in the hydrolysates originate from the degradation of the sugars (to furfural), of groups present in the hemicelluloses, of the lignin.

The presence of the inhibitors depends on the nature of the LVRM and on the conditions for its pretreatment.

In addition to the inhibition of the enzymes by furfural, combined effects of the various inhibitors have been noted.

As regards the simultaneous fermentation and hydrolysis according to the "SSF" ("Simultaneous Saccharification and Fermentation") process which consists in carrying out the enzymatic hydrolysis and the ethanolic fermentation in a single step, the main advantages thereof are the decrease in investments by eliminating the operations necessary for the enzymatic hydrolysis carried out beforehand, and the absence of cellulase inhibition by glucose, which is consumed by the fermentative microorganisms as it appears.

This results in an increase in the levels and rates of hydrolysis and in the overall ethanol or bioethanol productivities.

Moreover, the risks of microbial contamination of the glucose-rich hydrolysate are reduced.

However, it has become apparent that the gains provided by the SSF process, in particular from the economic point of view, require certain aspects to be optimized, in particular the initial dry matter concentration in order to obtain high concentrations of ethanol.

SUMMARY OF THE INVENTION

In order to remedy these drawbacks, the invention aims to propose an improved process for producing bioethanol, or ethanol, comprising a pretreatment of the lignocellulosic vegetable raw material in order to separate the cellulose, and an enzymatic hydrolysis of the cellulose, which is characterized first of all by only partial elimination of the lignins, prior to the enzymatic hydrolysis step, so as to obtain a determined non-zero residual overall level T (expressed as % by weight) of lignins which is between two limit values, i.e. a level included within a determined range. For assaying the level T of the lignins, the re-deposited lignins are not taken into account, only the intrinsic lignins.

Indeed, surprisingly, it has been discovered that it is not total elimination of the lignins which makes it possible to achieve the best possible yield, i.e. a level T of enzymatic hydrolysis equal to 100%.

DETAILED DESCRIPTION OF THE INVENTION

More specifically, the process is characterized in that it comprises, prior to the enzymatic hydrolysis step, a step of partial elimination of the lignins so as to obtain a residual overall level of lignins (T), expressed as percentage by weight, which is non-zero and which is included in a range determined by a lower limit (Llow), and an upper limit (Lupp), respectively equal to 0.30% and 4%.

Preferably, the residual overall level of lignins (T) is included in a range determined by a lower limit (Llow) and an upper limit (Lupp), respectively equal to 0.35% and 3.5%.

More preferably, the residual overall level of lignins (T) is equal to approximately 1.65%.

Such a treatment of the cellulose so as to eliminate the lignins in order to achieve a lignin level as recommended above is, for example, carried out by means of a step of treating with sodium hydroxide, followed by a washing step intended to eliminate the residual sodium hydroxide before the enzymatic hydrolysis step.

According to another characteristic of the process according to the invention, in order to obtain conditions for acidification before the enzymatic hydrolysis, and in particular a pH of about 5, a "re-acidification" of the mixture is carried out by means of an acid with a determined pKa, and in particular by means of weak organic acids such as acetic acid and/or formic acid, and/or another weak acid such as citric acid.

According to one characteristic of the process, the step for re-acidification of the mixture is carried out by means of acetic acid and/or formic acid and/or citric acid.

According to one characteristic of the process, the step for re-acidification of the mixture is carried out by means of a mixture of acetic acid and formic acid which contains 0.2% of formic acid by weight and 0.4% of acetic acid by weight with respect to the dry material of cellulose.

After said re-acidification step, the pH of the mixture is preferably between 4 and 6, preferably between 4.5 and 5.5.

More preferably, after said re-acidification step, the pH of the mixture is equal to 5.

According to one characteristic of the process, the step for partial elimination of the lignins is carried out at a temperature between 80° C. and 85° C.

According to one characteristic of the process, the step for partial elimination of the lignins is carried out at atmospheric pressure.

Surprisingly, it has been demonstrated that the use of such acids makes it possible to obtain a maximum level of hydrolysis, contrary, for example, to the use of a strong acid such as sulphuric acid.

Furthermore, in the context of the CIMV processes mentioned above, such an industrial use of acetic acid and/or formic acid is particularly advantageous since these acids are already used and present in the industrial cycle for producing cellulose from LVRM.

Among the other advantages of the invention, it has been demonstrated that the overall efficiency of the process for producing ethanol or bioethanol is close, or virtually equal, to the production of the theoretical maximum level of ethanol from LVRM, and that, in addition, this efficiency is the same depending on whether the overall process first makes use of an enzymatic hydrolysis step according to the invention, and then of a fermentation step, or else whether a simultaneous hydrolysis and fermentation process is carried out (SSF process).

Such an identical efficiency is due to the fact that the enzymatic hydrolysis according to the invention does not produce fermentation inhibitors.

Furthermore, it has been demonstrated that the advantages of the process according to the invention (overall level of lignins and particular conditions of re-acidification) are not modified, i.e. are of the same nature and have the same values, regardless of the cellulases used, and in particular whether they are cellulases of greater or lesser efficiency.

By way of examples of test results:

EXAMPLE OF ENZYMES TESTED AND THEIR ACTIVITY

|  | Activities in U/ml of enzymatic solution | | | |
| --- | --- | --- | --- | --- |
|  |  | Beta- | Cellulase | |
|  | Xylanase | glucosidase | Endo | exo |
| Cellic CTec | 42 | 3827 | 11 +−/− 5 | 281 +/− 40 |
| Accellerase 1500 | 7 | 392 | 12 +/− 6 | 66 +/− 9 |
| AB (EL 2009060L) | 8 | 32 | 1 +/− 05 | 13 +/− 2 |
| AB (EL 2009096L) | 0 | 77 | 2 +/− 1 | 25 +/− 3 |

Enzyme used for the tests: Cellic Ctec and Cellic Ctec 2 ("new-generation" enzyme with an activity 40% greater than the 1st generation).

Hydrolysis conditions: Temperature equal to 50° C., pH between 4.5 and 5, concentration of enzymes equal to 42 U/g.

Figure 1:
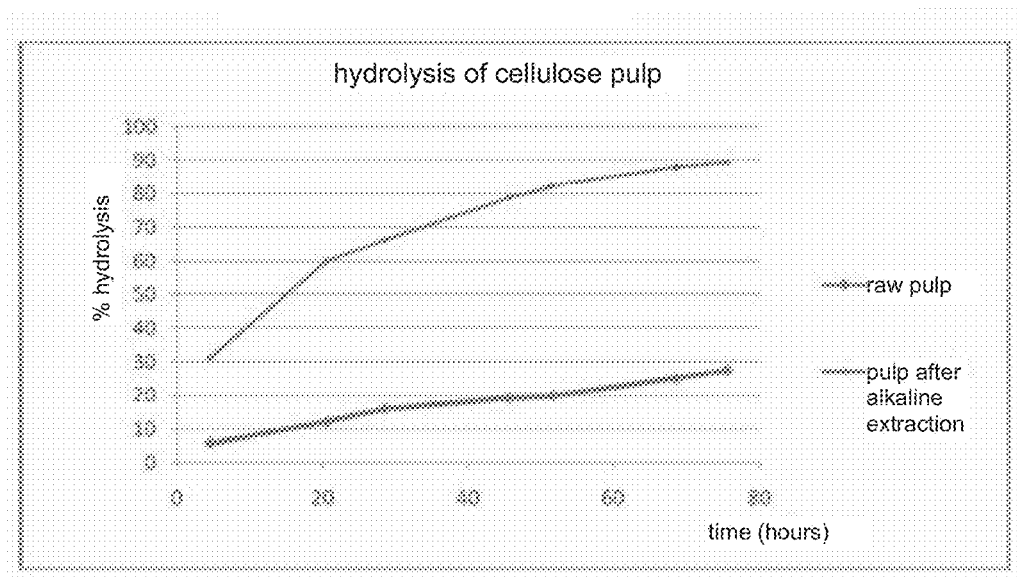
FIG. 1 shows the effect of an alkaline extraction on the level of hydrolysis of the cellulose.

Effect of an alkaline extraction on the level of hydrolysis of the cellulose: see FIG. 1, in which:

Raw pulp: pulp termed "CIMV" after extraction, delignification and washing;

Pulp after alkaline extraction: raw pulp treated at pH 12 at 85° C. for 1 hour.

Figure 2:
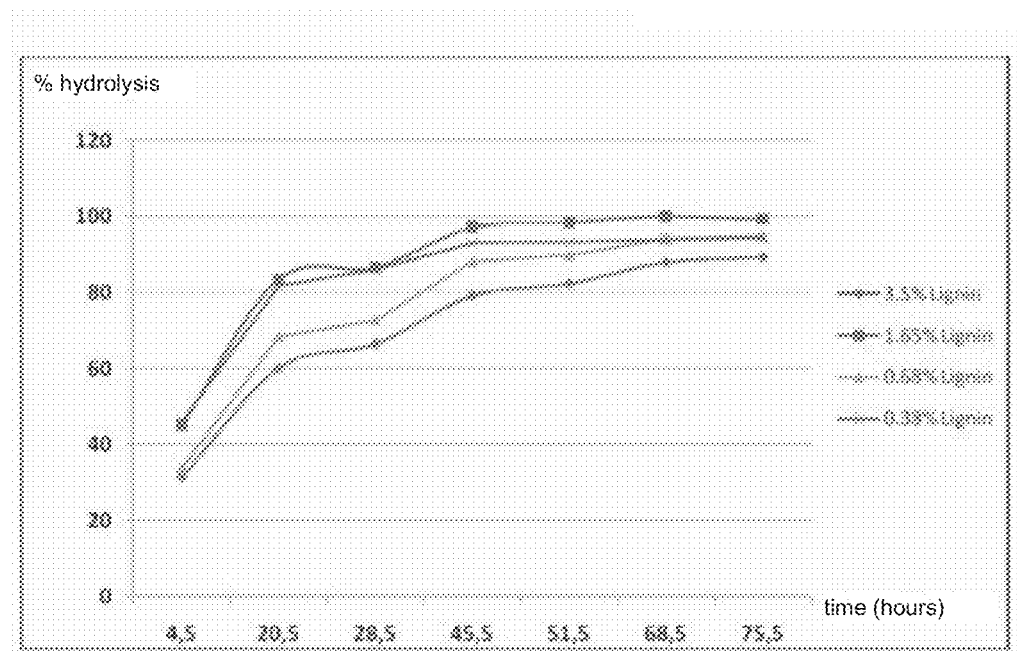
FIG. 2 shows the effect of the level of residual lignin on the hydrolysis of a cellulose pulp.

Effect of the level of residual lignin on the hydrolysis of a cellulose pulp: see FIG. 2.

Effect of the pKa of the acid used for acidification ("re-acidification") at pH 5 on the hydrolysis of the cellulose pulp:

|  | Acetic acid | Acetic acid + formic acid | Formic acid | Sulphuric acid |
| --- | --- | --- | --- | --- |
| % hydrolysis after 24 h | 95 | 80 | 78 | 45 |

The invention claimed is:

1. A process for producing bioethanol from a lignocellulosic vegetable raw material, comprising:
    (a) pretreatment of the lignocellulosic vegetable raw material in order to separate cellulose, hemicelluloses and lignins contained in the lignocellulosic vegetable raw material, the pretreatment comprising:
        (i) destructuring the lignocellulosic vegetable raw material by placing the material in the presence of a mixture comprising formic acid and water, at a reaction temperature between 95° C. and 110° C.;
        (ii) then, at atmospheric pressure and prior to any hydrolysis and fermentation action, separating:
        a solid phase comprising said cellulose and residual lignins; and
        a liquid phase, comprising a solution of water, the formic acid, the lignins and the hemicelluloses;
    (b) partial elimination of residual lignins from the solid phase so as to obtain a residual overall level of lignins in a range of 0.30% to 4% by weight;
    (c) enzymatic hydrolysis of said solid phase; and
    (d) alcoholic fermentation of products resulting from said enzymatic hydrolysis step to produce the bioethanol.

2. The process according to claim 1, wherein the residual overall level of lignins is in a range of 0.35% to 3.5% by weight.

3. The process according to claim 2, wherein the residual overall level of lignins is equal to approximately 1.65% by weight.

4. The process according to claim 1, wherein said step of partial elimination of residual lignins is carried out by a treatment with sodium hydroxide, followed by a washing step to remove residual sodium hydroxide before the enzymatic hydrolysis step.

5. The process according to claim 1, wherein in order to obtain conditions of acidification before the enzymatic hydrolysis step, the process comprises a step of re-acidification of the mixture, which is carried out by an acid, or a mixture of acids, of determined pKa.

6. The process according to claim 5, wherein said acid is acetic acid, formic acid, citric acid, or a mixture thereof.

7. The process according to claim 6, wherein said acid is a mixture of 0.4% by weight acetic acid and 0.2% by weight formic acid.

8. The process according to claim 5, wherein after said re-acidification step, the pH of the mixture is between 4 and 6.

9. The process according to claim 8, wherein after said re-acidification step, the pH of the mixture is between 4.5 and 5.5.

10. The process according to claim 9, wherein after said re-acidification step, the pH of the mixture is equal to about 5.

11. The process according to claim 1, wherein said step for partial elimination of the lignins is carried out at a temperature between 80° C. and 85° C.

12. The process according to claim 1, wherein said step for partial elimination of the lignins is carried out at atmospheric pressure.

13. A process for producing bioethanol from a lignocellulosic vegetable raw material, comprising:
    (a) pretreatment of the lignocellulosic vegetable raw material in order to separate cellulose, hemicelluloses and lignins contained in the lignocellulosic vegetable raw material, the pretreatment comprising:
        (i) destructuring the lignocellulosic vegetable raw material by placing the material in the presence of a mixture comprising formic acid and water, at a reaction temperature between 95° C. and 110° C.;
        (ii) then, at atmospheric pressure and prior to any hydrolysis and fermentation action, separating:
        a solid phase comprising said cellulose and residual lignins, and
        a liquid phase comprising a solution of water, formic acid, lignins and hemicelluloses;
    (b) partial elimination of the residual lignins from the solid phase by treating the solid phase with sodium hydroxide, so as to obtain a residual overall level of lignins in a range of 0.30% to 4% by weight,
    (c) re-acidification of the solid phase mixture from step (b) by treating the mixture with an acid, (d) enzymatic hydrolysis of said re-acidified solid phase mixture from step (c); and (d) alcoholic fermentation of products resulting from said enzymatic hydrolysis step to produce the bioethanol.

14. The process according to claim 13, wherein the partial elimination of the residual lignins comprises treating the solid phase with sodium hydroxide at a temperature of 80° C. to 85° C.

15. The process according to claim 13, further comprising a washing step to remove the sodium hydroxide before the re-acidification.

16. The process according to claim 13, comprising re-acidification of the solid phase mixture from step (b) by treating the mixture with acetic acid, formic acid, citric acid, or a mixture thereof.

* * * * *